(12) United States Patent
Dahlberg et al.

(10) Patent No.: US 9,534,980 B2
(45) Date of Patent: Jan. 3, 2017

(54) TEST METHOD AND APPARATUS FOR BIOREACTOR CONTAINERS HAVING RECEPTION SHEET CLAMPED BETWEEN BIOREACTOR CONTAINER AND BIOREACTOR CONTAINER COMPARTMENT

(75) Inventors: Martin Dahlberg, Bovenden (DE); Isabelle Gay, Peypin (FR); Lars Boettcher, Melsungen (DE); Stefan Obermann, Adelebsen (DE); Rainer Sandrock, Kassel (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 402 days.

(21) Appl. No.: 14/130,035

(22) PCT Filed: Jun. 26, 2012

(86) PCT No.: PCT/EP2012/002686
§ 371 (c)(1),
(2), (4) Date: Mar. 7, 2014

(87) PCT Pub. No.: WO2013/000565
PCT Pub. Date: Jan. 3, 2013

(65) Prior Publication Data
US 2014/0165707 A1 Jun. 19, 2014

(30) Foreign Application Priority Data

Jun. 30, 2011 (DE) .......................... 10 2011 106 165

(51) Int. Cl.
*G01M 3/04* (2006.01)
*G01M 3/32* (2006.01)
*C12M 1/34* (2006.01)

(52) U.S. Cl.
CPC .............. *G01M 3/32* (2013.01); *C12M 41/00* (2013.01); *G01M 3/329* (2013.01)

(58) Field of Classification Search
CPC ...... G01M 3/32; G01M 3/3218; C12M 23/14; C12M 23/42; C12M 23/44; C12M 23/46; C12M 23/24; C12M 25/06
(Continued)

(56) References Cited

U.S. PATENT DOCUMENTS 4,805,445 A 2/1989 Grappe
5,072,623 A 12/1991 Hendershot
(Continued)

FOREIGN PATENT DOCUMENTS

DE 695 09 833 1/2000
DE 10 2007 057 944 6/2009
(Continued)

OTHER PUBLICATIONS

European Patent Appl. No. 12 735 089.0—Office action issued Aug. 14, 2015.
(Continued)

*Primary Examiner* — Benjamin Schmitt
(74) *Attorney, Agent, or Firm* — Gerald E. Hespos; Michael J. Porco; Matthew T. Hespos (57) ABSTRACT

A method for testing the integrity of a bioreactor container includes providing a bioreactor container having a fluid-tight, at least locally flexible wall and having at least one container opening and providing a test apparatus having a bioreactor container compartment and a fluid-permeable and/or structured reception sheet arranged replaceably on the bioreactor container compartment. The method continues by arranging the bioreactor container in the bioreactor container compartment so that the bioreactor container wall contacts the reception sheet in the bioreactor container compartment, connecting the container opening of the bioreactor container to a fluid source filling the bioreactor container with a fluid from the fluid source to generate a
(Continued)

predetermined positive pressure $P_1$ in the bioreactor container at a first time $T_1$ and determining whether the bioreactor container is sufficiently leaktight.

17 Claims, 3 Drawing Sheets

(58) Field of Classification Search
USPC .................................................. 73/40, 49.2
See application file for complete search history.

(56) References Cited

U.S. PATENT DOCUMENTS

| | | | | |
|---|---|---|---|---|
| 5,205,157 | A * | 4/1993 | McDaniel | G01M 3/3281 73/49.2 |
| 5,668,534 | A * | 9/1997 | Haboian | G01M 3/32 340/604 |
| 6,205,847 | B1 * | 3/2001 | Nomoto | B65D 1/0215 73/49.2 |
| 2007/0220956 | A1 * | 9/2007 | Terentiev | G01M 3/187 73/49.2 |
| 2009/0188211 | A1 * | 7/2009 | Galliher | B01F 13/0827 53/434 |
| 2010/0326172 | A1 * | 12/2010 | Voute | G01M 3/3218 73/40.7 |
| 2011/0207218 | A1 * | 8/2011 | Staheli | B01F 3/04241 435/394 |

FOREIGN PATENT DOCUMENTS

| | | |
|---|---|---|
| EP | 0 060 548 | 9/1982 |
| EP | 0 209 203 | 1/1987 |
| EP | 1 283 061 | 2/2003 |
| WO | 95/00827 | 1/1995 |
| WO | 03 023351 | 3/2003 |
| WO | 2009/093995 | 7/2009 |
| WO | 2011/064067 | 6/2011 |

OTHER PUBLICATIONS

Divisional European Patent Appl. No. 15 001 756.4—Office action issued Aug. 17, 2015.
International Search Report Dated Oct. 2, 2012.
German Office Action dated Mar. 28, 2012.
Translation International Preliminary Report on Patentability.

* cited by examiner

TEST METHOD AND APPARATUS FOR BIOREACTOR CONTAINERS HAVING RECEPTION SHEET CLAMPED BETWEEN BIOREACTOR CONTAINER AND BIOREACTOR CONTAINER COMPARTMENT

BACKGROUND

1. Field of the Invention

The present description relates to a method and an apparatus for nondestructive testing of the integrity of bioreactor containers, and to a use of a fluid-permeable and/or structured reception sheet.

2. Description of the Related Art

In the pharmaceutical and biotechnology industries, flexible containers, for example bags, are used as bioreactor containers for processing or storage. The bioreactor containers may become damaged before actual use by the production process, transport or handling. It is therefore recommendable to carry out an integrity test of the bioreactor container before actual use. An integrity test is also expedient after use of the bioreactor container, in order to ascertain whether the integrity of the bioreactor container was maintained throughout the entire processing. The term "bioreactor container" in the context of the application therefore equally includes bioreactors and containers having locally flexible walls, which are used for example to receive, mix, store and dispense sterile media.

Conventional test methods for testing the integrity of a bioreactor container are the pressured drop method, flow measurement and trace gas analysis with the use of a test gas. A common feature of all the test methods is that a pressure difference is generated between the interior of the bioreactor container and a test apparatus containing the bioreactor container, or the surroundings of the bioreactor container. To this end, after production, or before and/or after use, the bioreactor container to be tested is arranged in a test apparatus for testing the integrity. This entails the risk that the bioreactor container to be tested will become damaged during the handling necessary for this, so that a leak is formed in the per se leaktight bioreactor container.

It is therefore an object of the invention to provide a method and an apparatus for testing the integrity of bioreactor containers, which allow improved integrity testing of the bioreactor container.

SUMMARY OF THE INVENTION

One aspect of the invention relates to a method for testing the integrity of a bioreactor container, having the steps:
  providing a bioreactor container having a fluid-tight, at least locally flexible wall and having at least one container opening;
  providing a test apparatus having a bioreactor container compartment and a fluid-permeable and/or structured reception sheet, which is arranged replaceably on the bioreactor container compartment;
  arranging the bioreactor container at least partially in the bioreactor container compartment, the bioreactor container coming in contact by its wall at least locally with the reception sheet in the bioreactor container compartment;
  connecting the at least one container opening of the bioreactor container to a fluid source;
  filling the bioreactor container with a fluid from the fluid source in order to generate a predetermined positive pressure $P_1$ in the bioreactor container at a first time $T_1$;
  determining whether the bioreactor container is sufficiently leaktight.

The determination may in this case be carried out in particular with the aid of a pressure difference (P2–P1) between a positive pressure P2 at a subsequent time T2 and the determined positive pressure at time T1. As an alternative or in addition, the determination may be carried out with the aid of a fluid quantity M which has been delivered to the bioreactor container after the time T1, in order to keep the positive pressure P1 constant. Furthermore, as an alternative or in addition, the determination may be carried out with the aid of detection of fluid substances or fluid particles, which have been delivered to the bioreactor container, outside or inside the bioreactor container. Advantageously, the accuracy of the determination or ascertainment and decision as to whether the bioreactor container is leaktight, can be increased when two or three of the quantities described above are detected. The probability that the leaktightness of the bioreactor container will be incorrectly classified or determined is thereby advantageously reduced.

An integrity test provides information about the integrity, or leaktightness, of the bioreactor container, in particular as to whether fluids can emerge from a leak or enter. In particular, the integrity is violated and the bioreactor container is unusable when microorganisms can enter the interior of the bioreactor container through a leak, so that the reaction inside the bioreactor container is compromised and the resulting products are unusable.

A bioreactor container comprises at least one fluid-tight wall, which is at least locally flexible. The term "bioreactor container" in the context of the invention equally includes bioreactors and containers having locally flexible walls, which are used for example to receive, mix, store and dispense sterile media. In this way, the bioreactor container is of variable volume. In other words, the internal volume of the bioreactor container can be increased by filling and decreased by emptying. Furthermore, the bioreactor container with the flexible wall can be applied at least locally onto the bioreactor container compartment, or onto the reception sheet arranged therein or thereon. For filling with and emptying a fluid, the bioreactor container has at least one container opening. The bioreactor container may be a sterile container, or sterile bioreactor container.

In the context of the application, the term "flexible" includes both plastic and elastic deformability. The term "fluid" includes a gaseous phase, a liquid phase and also a mixture of liquid and gaseous phases of a substance.

The wall of the bioreactor container consists of a fluid-tight material which is biologically and chemically inert with respect to the reaction to be carried out, that is to say the wall itself essentially does not react in the biological or chemical sense during the reaction. Preferably, the wall comprises a polymer, for example polyethylene (PE) and/or polypropylene (PP). More preferably, the bioreactor container is sterilizable, for example by means of steam, plasma treatment, gassing with ethylene oxide or gamma irradiation, so that the reaction can be started under sterile conditions. More preferably, the container openings are formed as sterile connectors or are fluidically connected to sterile connectors, for example through a tube.

The wall of the bioreactor container is at least locally formed flexibly. It is to be understood that the wall may be locally formed rigidly. Particularly in the region of the at least one container opening, the wall may essentially be formed rigidly so that the at least one container opening has a stable shape.

Bioreactors for carrying out a biological reaction may preferably have an internal volume of from about 5 milliliters to about 3000 liters, preferably about 2 liters, about 5 liters, about liters, about 50 liters, about 100 liters, about 250 liters, about 500 liters or about 1000 liters. Usually, during intended use, bioreactor containers are filled with an aqueous solution so that the content of the bioreactor container appropriately has a mass of from about 5 g to about 3000 kg. Since the walls of the bioreactor container cannot in general withstand the internal pressure which is generated by the mass of the content of the bioreactor container, bioreactor containers are generally arranged in the bioreactor container compartment of the bioreactor apparatus, and fastened therein. In this case, the wall of the bioreactor container bears at least locally on the wall of the bioreactor container compartment of the bioreactor apparatus, so that the bioreactor container compartment of the bioreactor apparatus supports the wall of the bioreactor container. The walls of such bioreactor container compartments of bioreactor apparatuses are usually formed from smooth stainless steel, in order to make contamination more difficult and to facilitate cleaning. Furthermore, the bioreactor container compartment of the bioreactor apparatus corresponds to the bioreactor container compartment of the test apparatus, the two bioreactor container compartments preferably being the same when the integrity test can be carried out while the bioreactor container is arranged in the bioreactor apparatus.

If an integrity test is then carried out after the bioreactor container has been arranged in the bioreactor container compartment (of the test apparatus or of the bioreactor apparatus), the interior of the bioreactor container being filled with a fluid in order to generate a positive pressure relative to the surroundings, the wall of the bioreactor container compartment could cover, or seal, a possibly existing leak in the wall of the bioreactor container.

However, a fluid-permeable and/or surface-structured reception sheet is arranged at least locally in or on the bioreactor container compartment. This means that the reception sheet is at least locally fluid-permeable, or a surface of the reception sheet is formed with a structure. In this case, the reception sheet is fluid-permeable in particular on a contact surface which is configured to come in contact with the bioreactor container, and is preferably fluid-permeable in a direction perpendicular to the contact surface. The reception sheet may preferably comprise an open-pored foam material, for example of polyurethane. More preferably, the reception sheet may consist of an essentially incompressible material which is not deformed by the reception of the bioreactor container, for example hard foam materials, sintered materials, in particular of metal, porous ceramic or fluid-permeable plastics. The compression modulus of the reception sheet is preferably more than 106 N/m2 or more than 109 N/m2.

More preferably, the reception sheet is formed in one piece and consists, in particular, of a homogeneous material. By virtue of the one-piece reception sheet, the inner surface of the bioreactor container compartment can advantageously be lined essentially fully, a bioreactor container received in the bioreactor container compartment coming in contact with the (flexible) wall of the bioreactor container compartment not directly, but merely indirectly via the reception sheet. More preferably, the flexible wall of the bioreactor container does not come in contact with any other parts of the bioreactor container compartment besides the reception sheet.

In particular, that surface of the reception sheet which comes in contact with the wall of the bioreactor container when the method is carried out is structured. Preferably, the wall of the bioreactor container compartment is covered fully by the reception sheet. The reception sheet is preferably arranged or fastened replaceably on or in the bioreactor container compartment, so that the reception sheet can be replaced easily if it is soiled.

Advantageously, the bioreactor container may bear indirectly on the wall of the bioreactor container compartment via the reception sheet, the result of the integrity test not being influenced by this since sealing of existing leaks of the bioreactor container by the wall of the bioreactor container compartment is avoided. This advantageously permits an improved integrity test, by which leaks in the wall of the bioreactor container can be determined with greater reliability, since it avoids a leak being inadvertently closed during the integrity test.

In particular, an integrity test can be carried out when the bioreactor container compartment belongs to a bioreactor apparatus with which the actual reaction is subsequently carried out. The integrity test can therefore advantageously be carried out "in situ", preferably before and/or after the reaction to be carried out, without having to handle the bioreactor container, for example in order to bring the bioreactor container into an integrity test apparatus.

The determination of whether the bioreactor container is sufficiently leaktight may be carried out by means of the pressure drop method, by measuring the fluid delivery rate at constant pressure, or by means of a test gas as the fluid. The test gas is expediently a gas which does not occur, or occurs only in traces, in the atmosphere, and can therefore be detected easily at the leak sites by means of a gas detector. The positive pressure P1 of the fluid inside the bioreactor container relative to the atmospheric pressure is between about 20 mbar and about 500 mbar, preferably between about 50 mbar and about 300 mbar.

The reception sheet is preferably porous, or comprises a porous material, the pore volumes expediently being connected to one another in such a way that the reception sheet is fluid-permeable. More preferably, the fluid-permeable reception sheet may have a direction-dependent, or anisotropic, fluid permeability. For example, the fluidic conductivity of the reception sheet in a direction parallel to a normal of the reception sheet surface may be greater than in a direction perpendicular to this normal, that is to say parallel to the extent of the reception sheet surface.

The fluid-permeable reception sheet may be made of metal. It may be a component of the wall of the bioreactor container compartment.

Preferably, the fluid-permeable reception sheet comprises a woven textile, a nonwoven textile and/or a foam material. Nonwovens, for example spun nonwovens of polypropylene, may be used as preferred materials for the reception sheet. Particularly for use in cleans rooms, the reception sheet may consist of a lint-free, or non-dusting, material which does not give off any particles into the surroundings. One exemplary nonwoven is for example Novatexx 2019 Viledon from the company Freudenberg Filtration Technologies KG, made of polypropylene with a weight of 17-100 g/m2 and an air permeability of 1000-5000 l/m2s at a pressure difference of 1 bar with a material thickness of 0.25-0.75 mm. Another exemplary material is available under the brand name Porex® XS49020-XS49100 from the company Porex Technologies GmbH. This material consists of polypropylene and polyethylene with a material thickness of from about 1.5 mm to about 5 mm, preferably more than about 3 mm. The size of the pores lies in the range of from about 20 µm to about 175 µm, preferably less than about 120 µm. The air permeability is from about 150 to about 300 l/cm2min with a 1.2 inch water column. It has proven advantageous to use a polymer material which contains thermally conductive additives, for example boron nitrite, for the fluid-permeable outer sheet. In this way, temperature control of the bioreactor container can advantageously be improved.

As an alternative or in addition, the reception sheet may be structured. In the context of the application, a structured reception sheet means that at least that surface of the reception sheet which comes in contact with the bioreactor container during intended use is not smooth but has a structure, or a relief. In particular, the structure may be formed by elevations and depressions which are produced by variation of the material thickness of the reception sheet. That is to say, the reception sheet has a greater material thickness in the region of elevations than in the region of depressions. As an alternative, the material thickness of the reception sheet may be essentially constant, the structure being molded into the material. In this case, in particular, the flexibly formed region of the wall is provided with a structured reception sheet. Preferably, however, rigid regions of the wall may also have a structured reception sheet.

The structured reception sheet may be fluid-impermeable, so that the reception sheet can advantageously fulfil an additional sealing function in order to protect the bioreactor container compartment against contamination by fluids emerging from a leak. The structured reception sheet leads to an equivalent technical effect as a fluid-permeable reception sheet in the sense that a leak in the inner sheet cannot be externally sealed by means of an object. Owing to the structure of the reception sheet, an object cannot in general join fluid-tightly with the reception sheet in such a way that a fluid emerging from the bioreactor container would not reach the surroundings. In particular, such sealing cannot take place by means of the bioreactor container compartment. Accordingly, an integrity test can be carried out by applying a positive pressure to the bioreactor container, a pressure drop or a fluid flow due to the leak being detectable and making it possible to deduce that there is a leak.

When an integrity test of the bioreactor container is carried out in the bioreactor container compartment, the wall of the bioreactor container is pressed against the structured reception sheet. The effect of the structure of the reception sheet is that channels conveying fluid are formed between the two. In this way, a fluid emerging through a leak can be delivered into the surroundings through the channels conveying fluid, so that the leak in the wall of the bioreactor container cannot be sealed by the wall of the bioreactor container compartment. As already described above, this advantageously permits an improved integrity test by which leaks in the wall of the bioreactor container can be determined with greater reliability, since it avoids a leak being inadvertently closed during the integrity test, and furthermore the integrity test of the bioreactor container can advantageously be carried out "in situ" before and/or after the experimental run, or the production process.

Preferably, the structured reception sheet has depressions which are at least about 100 µm deep. In this case, two neighboring depressions define, or form, an elevation. Likewise, at least two neighboring elevations define, or form, a depression. More preferably, the depressions have at least a depth of more than about 150 µm, more preferably more than about 250 µm, and in particular more than about 500 µm, relative to the neighboring elevations. This ensures release of the fluid emerging from a leak into the surroundings.

Preferably, the structured reception sheet has elevations which are at most about 200 µm wide. More preferably, the elevations have a width of less than about 150 µm, more preferably less than about 100 µm, and in particular less than about 50 µm. This prevents the possibility that an elevation can be positioned with an accurate fit on a leak and that the leak can thereby be sealed by a single elevation. The expected diameter of a leak is from about 5 µm to about 1000 µm.

Preferably, the elevations and/or depressions of the structured reception sheet are oriented along a preferential direction V. In particular, the elevations and/or depressions extend essentially along a longitudinal direction, neighboring elevations and/or depressions being oriented parallel to one another. The preferential direction V in this case corresponds to the longitudinal direction along which the elevations or depressions extend. In other words, the elevations and depressions may in particular form a groove structure or a rhombic structure on the reception sheet.

Preferably, the provision of the bioreactor container compartment and of the fluid-permeable or structured reception sheet involves the reception sheet being arranged on or in the bioreactor container compartment. For example, the bioreactor container compartment may be lined with the reception sheet. In particular, the reception sheet may be provided already in a shape congruent with the bioreactor container compartment, so that the reception sheet merely needs to be placed into the bioreactor container compartment, the bioreactor container compartment in particular essentially not being separated from the reception sheet. In order to achieve congruence of the reception sheet shape, the reception sheet may be assembled from a plurality of parts, for example by adhesive bonding, welding or stitching.

Preferably, the method comprises the subsequent steps:
  filling the bioreactor container with reactants;
  carrying out a chemical or biochemical reaction in the bioreactor container;
  releasing the content from the bioreactor container.

Advantageously, the integrity test may be integrated into the production method, since the bioreactor container can be filled with the reactants, or starting substances of the reaction, directly following the integrity test. In order to remove the rest of the fluid used for the integrity test from the bioreactor container, the starting substances may expediently be delivered through a container opening located underneath on the bioreactor container, while the fluid is vented through a container opening located above, in particular through a sterile filter. Particularly in the case of starting substances containing protein, foaming is advantageously avoided.

Preferably, the determination of whether the bioreactor container is sufficiently leaktight is performed before and/or after the biochemical reaction is carried out in the bioreactor container. In other words, the method preferably comprises the steps following release:
  connecting the at least one container opening of the bioreactor container to a fluid source;
  filling the bioreactor with a fluid from the fluid source, in order to generate a predetermined positive pressure $P_1$ in the bioreactor container at a first time $T_1$, the wall of the bioreactor container coming in contact at least locally with the reception sheet of the bioreactor container compartment;

determining whether the container is sufficiently leaktight.

The connection of the at least one container opening of the bioreactor container is carried out with the fluid source is preferably carried out via a sterile filter.

The determination may, as already described above, be carried out with the aid of a pressure difference ($P_2-P_1$) between a positive pressure $P_2$ at a subsequent time $T_2$ and the determined positive pressure at time $T_1$, or with the aid of a fluid quantity M which has been delivered to the bioreactor container after the time $T_1$, in order to keep the positive pressure $P_1$ constant, or with the aid of detection of fluid substances or fluid particles, which have been delivered to the bioreactor container, outside or inside the bioreactor container.

In other words, after the end of the reaction a subsequent integrity test may be carried out in order to check whether the bioreactor container has retained its integrity throughout the entire time of the reaction.

The invention also relates to an apparatus for testing the integrity of a bioreactor container, comprising:

a bioreactor container compartment for receiving a bioreactor container;

at least one fluid-permeable and/or structured reception sheet which is replaceably arranged at least partially on the bioreactor container compartment, the reception sheet being configured in order to be arranged at least locally between a wall of the bioreactor container and the bioreactor container compartment.

The bioreactor container compartment is essentially rigid. A bioreactor container can be introduced into the bioreactor container compartment along an introduction direction E, and is received by the bioreactor container compartment in such a way that further displacement of the bioreactor container along the introduction direction E, and preferably also perpendicularly to the introduction direction E, is prevented. More preferably, the bioreactor container compartment limits the volumetric extent of the bioreactor container during or after its filling. Preferably, the bioreactor container compartment has at least one viewing opening, through which the bioreactor container in the bioreactor container compartment is visible. The viewing opening may be formed as a through-opening in the wall of the bioreactor container compartment. As an alternative, the viewing opening may be closed by a transparent material. Advantageously, the bioreactor container, and in particular the interior of the bioreactor container, can be visually inspected continuously in the closed state during intended use.

Preferably, the fluid-permeable and/or structured reception sheet is arranged that region of the wall of the bioreactor container compartment which during intended use comes in contact with the bioreactor container, or which receives the wall pressure of the bioreactor container. In particular, the wall of the bioreactor container compartment is fully covered by the fluid-permeable and/or structured reception sheet. In other words, the bioreactor container is received indirectly via the reception sheet in the bioreactor container compartment.

The reception sheet is arranged or fastened replaceably on the bioreactor container compartment. Advantageously, the reception sheet can be replaced straightforwardly in the event of contamination. The fastening of the reception sheet may be carried out by fastening means which are fastened on the reception sheet, and are in force fit or engagement with complementary fastening means of the bioreactor container compartment. For example, the reception sheet and the bioreactor container compartment may have complementary parts of a hook-and-loop fastener. As an alternative or in addition, the bioreactor container compartment may have projections which engage in openings of the reception sheet. As an alternative or in addition, the reception sheet may have a collar which can be fitted over an edge region of the bioreactor container compartment. Regarding preferred materials of the reception sheet, reference is made to the description of the method.

Preferably, the apparatus comprises a fluid source, which can be connected fluidically to a container opening of the bioreactor container. After the at least one container opening of the bioreactor container has been connected to the fluid source, the bioreactor container can be filled with a fluid from the fluid source, in order to generate a predetermined positive pressure P1 in the bioreactor container. Owing to the positive pressure P1, the wall of the bioreactor container is pressed against the wall of the bioreactor container compartment so that the reception sheet is firmly clamped, or firmly pressed, at least locally between the bioreactor container and the bioreactor container compartment.

Preferably, the apparatus comprises a pressure sensor which can record the fluid pressure inside the bioreactor container. Preferably, the fluid source and the pressure sensor may be arranged together in a testing device. The testing device can in particular be an automatic testing device, which carries out the regulation of the fluid source and the recording of the pressure by means of the pressure sensor automatically or with computer assistance.

Furthermore, the testing device can preferably determine whether the bioreactor container (1) is sufficiently leaktight. In this case, the determination may be carried out in particular with the aid of a pressure difference (P2−P1) between a positive pressure P2 at a subsequent time T2 and the determined positive pressure P1 at time T1, the pressure being recorded by the pressure sensor. As an alternative or in addition, the determination may be carried out with the aid of a fluid quantity M which had to be delivered to the bioreactor container (1) after the time T1, in order to keep the positive pressure P1 constant. Expediently, the test apparatus also comprises a fluid quantity recording device which records the quantity of fluid which is delivered to the bioreactor container. As an alternative or in addition, fluid substances or fluid particles, which have been delivered to the bioreactor container, may be detected outside or inside the bioreactor container. Expediently, the bioreactor container is then filled with a test gas, in which case the test apparatus may also preferably comprise a gas detector which is sensitive to traces of this test gas. It is to be understood that an external gas detector may also be provided.

One aspect relates to a use of a fluid-permeable and/or structured reception sheet for replaceable arrangement on a bioreactor container compartment, wherein after a bioreactor container has been arranged in the bioreactor container compartment, the reception sheet is at least locally clamped firmly by the bioreactor container and the bioreactor container compartment between them.

In other preferred embodiments of the invention, the fluid-permeable reception sheet comprises a woven textile, a nonwoven textile and/or a foam material. In other preferred embodiments of the invention, the structured reception sheet has depressions which are at least about 100 µm deep and/or the structured reception sheet has elevations which are at most about 200 µm wide. The preferred embodiments of the invention relate in particular to embodiments of the method, the apparatus and the use.

Preferred embodiments of the present invention will be explained by way of example below with the aid of the appended drawings. Individual features of the preferred embodiments presented may be combined to form other preferred embodiments.

DETAILED DESCRIPTION OF THE PREFERRED EMBODIMENTS

Figure 1:
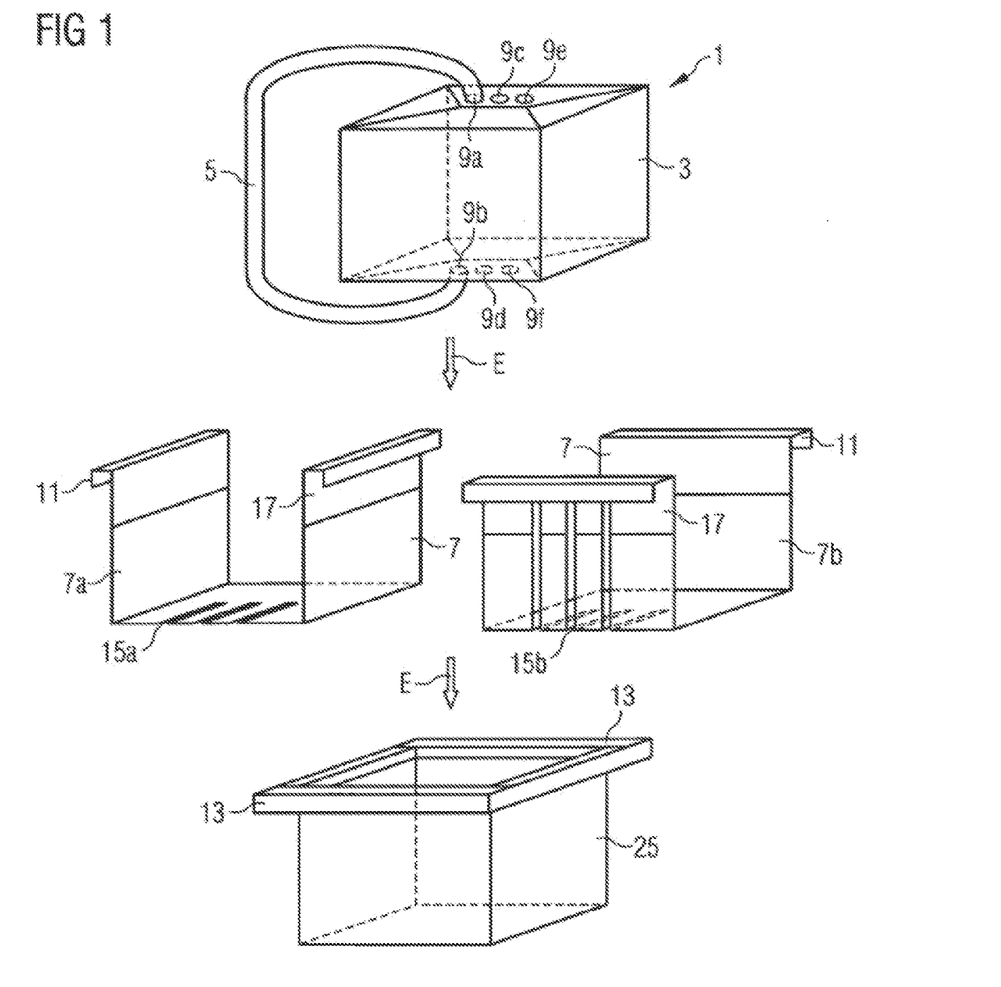
FIG. 1 shows a perspective view of a bioreactor container and a bioreactor container compartment.

FIG. 1 shows one preferred embodiment of a bioreactor container 1 of a bioreactor container compartment 25 in a perspective view. The bioreactor container 1 is in particular a flexible container, for example a bag, which can be used for processing or storage of biotechnology products. The bioreactor container 1 may have locally flexible walls. For example, a bioreactor container 1 may be a fermenter. The bioreactor container 1 is preferably used to receive, mix, store and dispense sterile media. In particular, the bioreactor container 1 may be configured in order to receive and deliver fluids under sterile conditions, for example by means of suitable sterile filters.

The bioreactor container 1 shown has a box-like or cuboid shape. It is to be understood that the bioreactor container 1 may also have a tetrahedral, cylindrical, spherical, prismatic or other desired shape. Accordingly, it should be noted that in the context of the invention, the term "bioreactor container" equally includes bioreactors and containers having locally flexible walls, which are used for example to receive, mix, store and dispense sterile media. The bioreactor container 1 comprises a fluid-impermeable flexible wall 3, which preferably consists of a film, or a laminate of a plurality of films. In other words, the wall 3 may be formed essentially as a flexible bag, which can vary in shape.

The internal volume of the bioreactor container 1 is fluidically connectable or connected via the container openings 9a, 9b, 9c, 9d, 9e, 9f to the surroundings or to further elements, for example fluid lines. It is to be understood that the fluid-impermeable flexible wall 3 may be formed more stiffly, or rigidly, in the region of the container openings 9a, 9b, 9c, 9d, 9e, 9f, so that the 9a, 9b, 9c, 9d, 9e, 9f have a stable shape and glands or connectors optionally connected thereto remain leaktight. Two of the container openings 9a, 9b may be fluidically connected to one another by a fluid line 5, so that circulation of the content of the bioreactor container 1 by transport of fluid from one of the container openings 9b to the other one of the container openings 9a through the fluid line 5 is possible. The circulation is preferably carried out by means of a circulation pump (not shown). Through the remaining container openings 9c, 9d, 9e, 9f, the bioreactor container 1 may for example be filled and emptied.

The bioreactor container compartment 25 shown in FIG. 1 is essentially rigid and preferably made of a corrosion-resistant material, for example stainless steel. A fluid-permeable and/or structured reception sheet 7 can be inserted into the bioreactor container compartment 25 along an introduction direction E, the reception sheet 7 in the embodiment shown comprising two layers 7a, 7b, which can be arranged above one another. The bioreactor container 1 can likewise be introduced along the introduction direction E into the bioreactor container compartment 25. After introduction, the bioreactor container 1 is received by the bioreactor container compartment 25 in such a way that further displacement of the bioreactor container along the introduction direction E, and also perpendicularly to the introduction direction E, is prevented. The rigid bioreactor container compartment 25 furthermore limits the volumetric extent of the bioreactor container 1 during or after its filling.

After the reception sheet 7 and the bioreactor container 1 have been arranged in the bioreactor container compartment 25, the reception sheet 7 is at least locally clamped firmly between the bioreactor container compartment 25 and the wall 3 of the bioreactor container 1, in particular owing to the pressure which the bioreactor container 1 exerts on the bioreactor container compartment 25. Preferably, the reception sheet 7 is arranged in the bioreactor container compartment 25 in such a way that the wall 3 of the bioreactor container 1 does not come directly in contact with the bioreactor container compartment 25 during intended use, that is to say in particular after the bioreactor container 1 has been filled with a fluid. On the other hand, the bioreactor container 1 comes in contact with the reception sheet 7. In particular, those walls of the bioreactor container compartment 25 which face toward the bioreactor container 1 are fully covered by the fluid-permeable and/or structured reception sheet 7.

The reception sheet 7 is arranged, or fastened, replaceably on the bioreactor container compartment 25, so that the reception sheet 7 can be replaced straightforwardly. The fastening of the reception sheet 7 may be carried out by fastening means which are fastened on the reception sheet 7, and are in force fit or engagement with complementary fastening means of the bioreactor container compartment 25. The embodiment of the reception sheet 7 as shown in FIG. 1 has a collar 11 which can be fitted over an edge region 13 of the bioreactor container compartment 25. The collar 11 may, for example, be held in its position on the edge region 13 of the bioreactor container compartment 25 by a material tension in the reception sheet 7, for example by a region of the reception sheet 7 which is configured to be elastically extensible, or by a rubber band. As an alternative or in addition, the reception sheet 7 may be connected releasably to the bioreactor container compartment 25 by further fastening means. Hook-and-loop fasteners have proven to be preferred fastening means.

The reception sheet 7 may be formed in one piece or as shown in FIG. 1, may be assembled from a plurality of parts or layers 7a, 7b. Depending on the shape of the bioreactor container compartment 25, a one-piece or multi-piece reception sheet 7 may present easier handling. In the embodiment of the reception sheet 7 shown in FIG. 1, two rectangular layers 7a, 7b are introduced crosswise above one another into the bioreactor container compartment 25 along the introduction direction E, so that the collar 11 can be fitted straightforwardly over the edge region 13. The reception sheet 7 may, in particular, have access openings 15a, 15b. The access openings 15a, 15b may be round openings or slots, so that for example a fluid line 5 can be passed through the reception sheet 7 to one of the container openings 9a to 9f.

Irrespective of the external shape, the reception sheet 7 may be configured rigidly or flexibly. Advantageously, a flexible reception sheet 7 makes it possible for the reception sheet 7 to be straightforwardly folded and stored compactly. The reception sheet 7 may also only locally be formed rigidly, or formed more stiffly than in other regions. For example, a reinforcement region 17 may be provided in the region of the collar 11 and/or in the region of the access openings 15a, 15b.

Figure 2A:
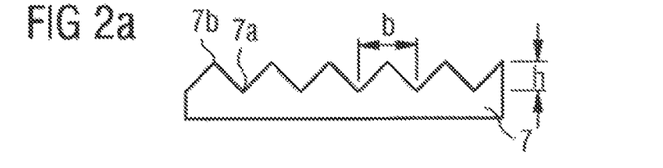
FIG. 2a shows a section through one embodiment of a structured reception sheet.
Figure 2B:
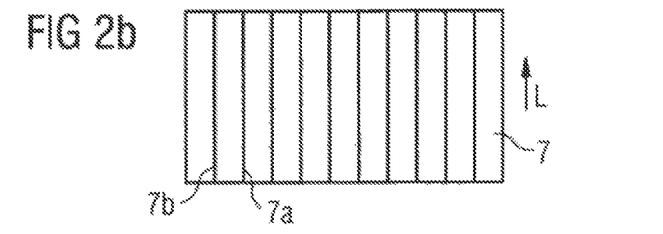
FIG. 2b shows a plan view of the structured reception sheet.

FIG. 2a shows a section through, and FIG. 2b shows a plan view of, one embodiment of a structured reception sheet 7. In this embodiment, the reception sheet 7 has depressions 7a and elevations 7b, which extend parallel to one another along a longitudinal direction L. In other words, the elevations 7b and depressions 7a form a groove structure on the reception sheet 7, or the outer surface. The elevations 7b and depressions 7a are formed by variation of the material thickness of the reception sheet 7. Preferably, the structured outer side comprises elevations which have a width b of at most about 200 µm, preferably about 50 µm, and a height h of at most about 200 µm, preferably about 50 µm.

Figure 3A:
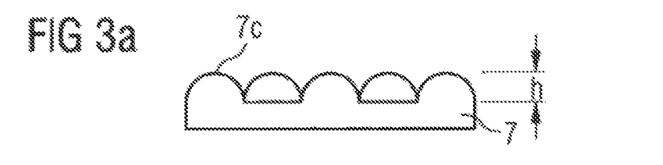
FIG. 3a shows a section through another embodiment of a structured reception sheet.
Figure 3B:
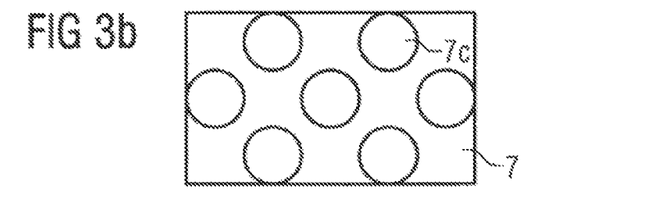
FIG. 3b shows a plan view of the structured reception sheet.

FIG. 3a shows a section through, and FIG. 3b shows a plan view of, one embodiment of a structured reception sheet 7. In this embodiment, the reception sheet 7 has hemispherical elevations 7c, or pimples 7c. The pimples 7c are preferably arranged regularly on the reception sheet 7. The elevations or pimples 7c preferably have a height h of at most about 200 µm. The point bearing should be less than 5 µm, preferably less than 2.5 µm, but at most half the diameter of the hole size to be detected.

Figure 4A:
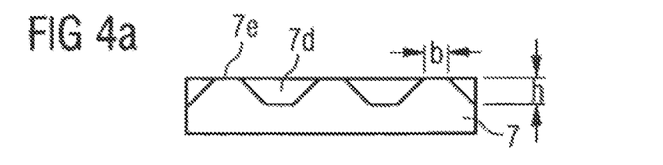
FIG. 4a shows a section through another embodiment of a structured reception sheet.
Figure 4B:
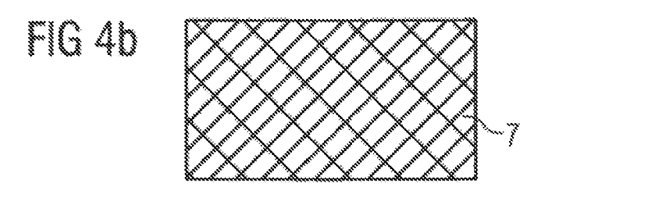
FIG. 4b shows a plan view of the structured reception sheet.

FIG. 4a shows a section through, and FIG. 4b shows a plan view of, one embodiment of a structured reception sheet 7. In this embodiment, the reception sheet 7 has depressions 7d and elevations 7e which form a rhombic structure on the reception sheet 7, or the surface thereof. The elevations 7e and depressions 7d are formed by variation of the material thickness of the reception sheet 7, the elevations having a width b of at most about 5 µm, preferably about 2.5 µm, and a height h of at least about 100 µm.

It is to be understood that the elevations and depressions of the reception sheet 7 need not form a regular or periodic pattern, but may form an unordered, irregular structure.

Figure 5:
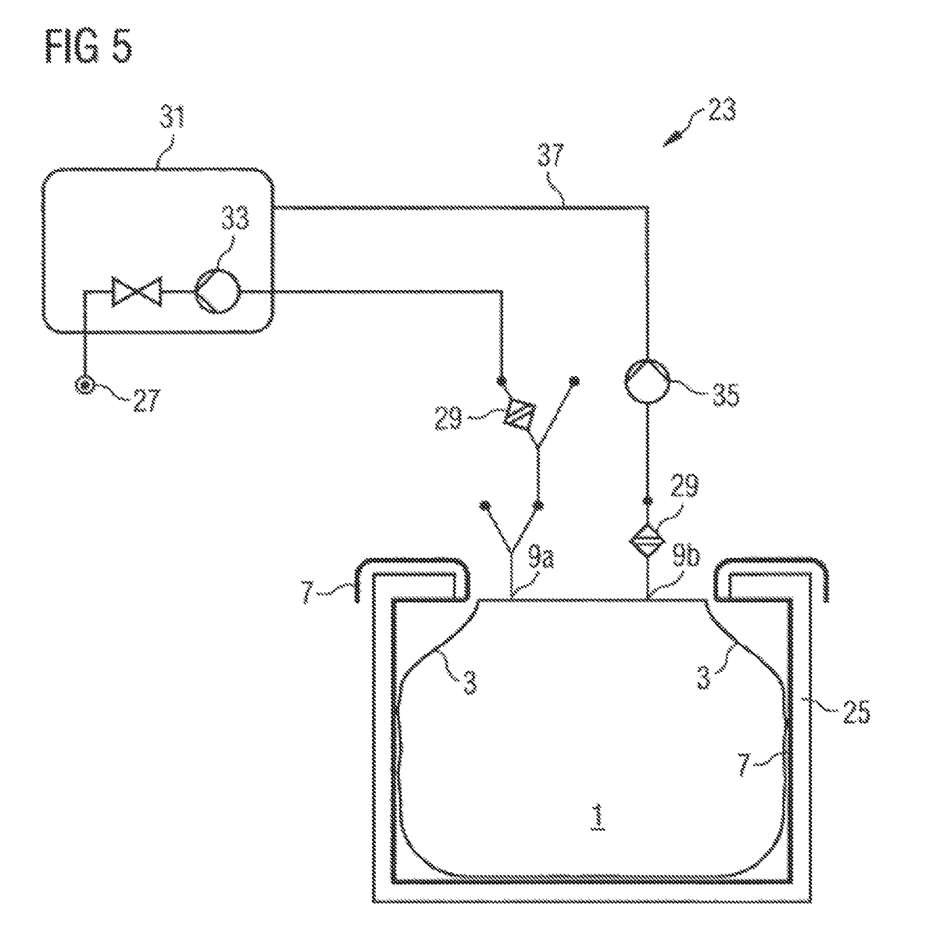
FIG. 5 shows a schematic view of an apparatus for testing the integrity of the bioreactor container.

FIG. 5 shows a schematic view of an arrangement 23 for testing the integrity of the bioreactor container 1. For the test, the bioreactor container 1 is arranged in a bioreactor container compartment 25 of a bioreactor apparatus. After arrangement, a reception sheet 7 lies between the bioreactor container compartment and a wall 3 of the bioreactor container 1. At least one container opening 9a of the bioreactor container 1 is fluidically connected to a fluid source 27, for example by means of a sterile filter 29 in order to keep the interior of the bioreactor container 1 sterile. The fluid source may be part of a test apparatus 31, for example Sartocheck® 4plus from Sartorius Stedim Biotech GmbH, or it may be an external fluid source 27.

The bioreactor 1 is filled with a fluid from the fluid source 27 at a time T1 with a predetermined positive pressure P1 of from about 50 mbar to about 100 mbar, the wall 3 of the bioreactor container 1 bearing at least locally on the reception sheet 7, and the latter is then pressed against the bioreactor container compartment 25. In this way, the reception sheet 7 is clamped firmly between the bioreactor container 1 and the bioreactor container compartment 25, the reception sheet 7 preventing direct contact of the bioreactor container 1 with the bioreactor container compartment 25.

The pressure difference P2−P1 between a positive pressure P2 at a subsequent time T2 and the determined positive pressure at time T1 may be detected by means of an internal pressure sensor 33 of the test apparatus 31, or by means of an external pressure sensor 35 which is fluidically connected to a container opening 9b. The external pressure sensor 35 is preferably connected to the test apparatus 31 via a signal line 37. With the aid of the pressure difference P2−P1, it is possible to determine whether the bioreactor container 1 is leaktight, or has integrity. To this end, the pressure difference must be less than a predetermined amount, in the ideal case equal to zero. Advantageously, the bioreactor container 1 may bear on the reception sheet 7 in the bioreactor container compartment 25 during the test, the result of the integrity test not being influenced since the sealing of leaks which exist by the reception sheet 7 is avoided.

The invention claimed is:

1. A method for testing the integrity of a bioreactor container (1), having the steps of:
   providing a bioreactor container (1) having a fluid-tight, at least locally flexible wall (3) and having at least one container opening (9a, 9b, 9c, 9d);
   providing a test apparatus having a bioreactor container compartment (25) and a fluid-permeable and/or structured reception sheet (7) that is arranged replaceably on the bioreactor container compartment (25);
   arranging the bioreactor container (1) at least partially in the bioreactor container compartment (25), the bioreactor container (1) coming in contact by its wall (3) at least locally with the reception sheet (7) in the bioreactor container compartment (25);
   connecting the at least one container opening (9a, 9b, 9c, 9d) of the bioreactor container to a fluid source (27);
   filling the bioreactor container (1) with a fluid from the fluid source (27) and thereby clamping the reception sheet (7) between the bioreactor container (1) and the bioreactor container compartment (25) and generating a predetermined positive pressure P1 in the bioreactor container (1) at a first time T1; and
   determining whether the bioreactor container (1) is sufficiently leaktight.

2. The method of claim 1, wherein the determination of whether the bioreactor container (1) is sufficiently leaktight is carried out with the aid of a pressure difference (P2−P1) between a positive pressure P2 at a subsequent time T2 and the determined positive pressure at time T1.

3. The method of claim 1, wherein the determination of whether the bioreactor container (1) is sufficiently leaktight is carried out with the aid of a fluid quantity M that has been delivered to the bioreactor container (1) after the time T1, in order to keep the positive pressure P1 constant.

4. The method of claim 1, wherein the determination of whether the bioreactor container (1) is sufficiently leaktight is carried out with the aid of detection of fluid substances that have been delivered to the bioreactor container (1), outside or inside the bioreactor container (1).

5. The method of claim 1, further comprising the steps of:
   filling the bioreactor container (1) with reactants;
   carrying out a chemical or biochemical reaction in the bioreactor container (1);
   releasing the content from the bioreactor container (1).

6. The method of claim 5, wherein the determination of whether the bioreactor container (1) is sufficiently leaktight is carried out before and after the biochemical reaction is carried out in the bioreactor container (1).

7. The method of claim 1, wherein the fluid-permeable reception sheet is a woven textile, a nonwoven textile and/or a foam material.

8. The method of claim 1, wherein the structured reception sheet has depressions that are at least about 200 μm deep and/or wherein the structured reception sheet has elevations that are at most about 200 μm wide.

9. The method of claim 1, wherein the bioreactor container compartment (25) has walls that face the bioreactor container (1), the walls of the bioreactor container compartment (25) that face toward the bioreactor container (1) being covered fully by the fluid-permeable and/or structured reception sheet (7).

10. The method of claim 1, further comprising fastening the reception sheet (7) replaceably on the bioreactor container compartment (25) prior to filling the bioreactor container (1) with the fluid from the fluid source (27).

11. An apparatus for testing the integrity of a bioreactor container, comprising:
 a bioreactor container compartment (25) for receiving a bioreactor container (1);
 at least one fluid-permeable and/or structured reception sheet (7) that is replaceably arranged at least partially on the bioreactor container compartment (25), the reception sheet (7) being configured to be arranged and clamped at least locally between a wall (3) of the bioreactor container (1) and the bioreactor container compartment (25).

12. The apparatus of claim 11, further comprising:
 a fluid source (27) that can be connected fluidically to a container opening (9a, 9b, 9c, 9d) of the bioreactor container (1).

13. The apparatus as claimed in claim 11, further comprising:
 a testing device (31), by which it is possible to determine whether the bioreactor container (1) is sufficiently leaktight.

14. The apparatus as claimed in claim 13, wherein the determination is carried out with the aid of at least one of:
 a pressure difference (P2−P1) between a positive pressure P2 at a subsequent time T2 and the determined positive pressure at time T1,
 a fluid quantity M that has been delivered to the bioreactor container (1) after the time T1, to keep the positive pressure P1 constant,
 and
 detection of fluid substances that have been delivered to the bioreactor container (1), outside the bioreactor container (1).

15. The apparatus of claim 11, wherein the fluid-permeable reception sheet is a woven textile, a nonwoven textile and/or a foam material.

16. The apparatus of claim 11, wherein the structured reception sheet has depressions that are at least about 200 μm deep and elevations that are at most about 200 μm wide.

17. The apparatus of claim 11, wherein the reception sheet (7) is fastened replaceably on the bioreactor container compartment (25).

* * * * *